United States Patent [19]

Sullivan

[11] Patent Number: 5,655,592
[45] Date of Patent: Aug. 12, 1997

[54] METHOD AND DEVICE FOR ELIMINATING COMPRESSION AND DISTORTION OF WAX PATTERNS IN LOST-WAX CASTING

[75] Inventor: Michael R. Sullivan, Attleboro, Mass.

[73] Assignee: Leach & Dillon, Inc., North Attleboro, Mass.

[21] Appl. No.: 315,415

[22] Filed: Sep. 29, 1994

[51] Int. Cl.$^6$ .............................. B22C 9/04; A61C 13/20
[52] U.S. Cl. .................. 164/456; 164/35; 164/151.4; 164/237; 164/376; 249/54; 249/62
[58] Field of Search ................ 164/34, 35, 4.1, 164/456, 516, 150.1, 151.4, 237, 376; 249/54, 61, 62

[56] References Cited

U.S. PATENT DOCUMENTS 5,183,095   2/1993   Sullivan ................................. 164/34

FOREIGN PATENT DOCUMENTS

| 56-168934 | 12/1981 | Japan | 164/456 |
| 57-72748 | 5/1982 | Japan | 164/516 |
| 3-198943 | 8/1991 | Japan | 164/4.1 |
| 4-158949 | 6/1992 | Japan | 164/456 |
| 728978 | 4/1980 | U.S.S.R. | 164/4.1 |

*Primary Examiner*—J. Reed Batten, Jr.
*Attorney, Agent, or Firm*—Phillips, Lytle, Hitchcock, Blaine & Huber

[57] ABSTRACT

Compression and distortion on a wax pattern during curing are eliminated by employing a thermochromatic dye which changes color when investment material sets. By monitoring the dye, the set investment material can be removed from the assembly before curing, eliminating compression forces on the wax pattern from the exothermic curing process expanding the investment material against the constraints of the assembly.

8 Claims, 1 Drawing Sheet

U.S. Patent  Aug. 12, 1997  5,655,592
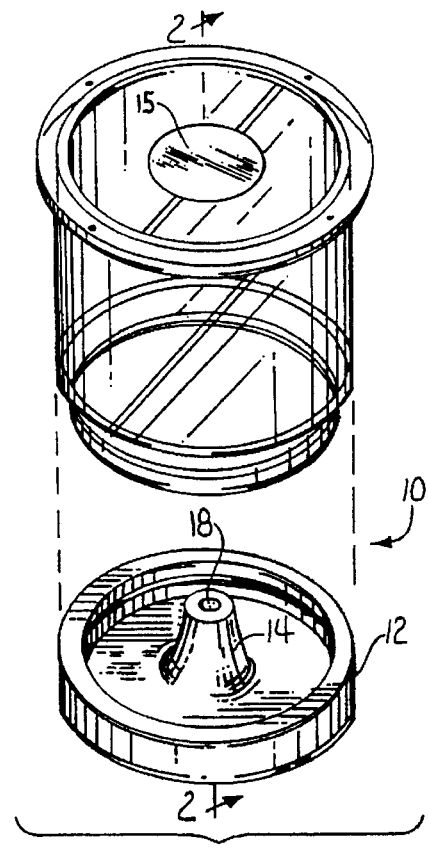
FIG. 1.
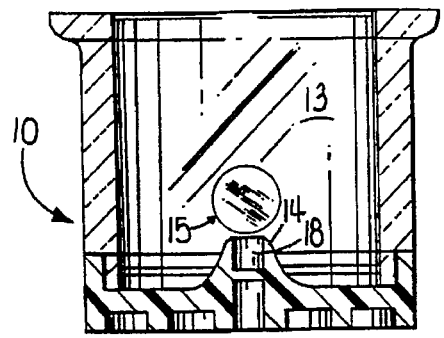
FIG. 2.
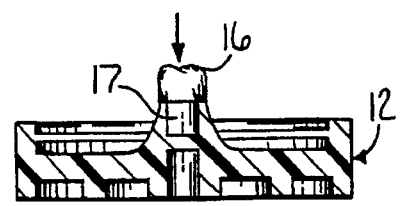
FIG. 3.
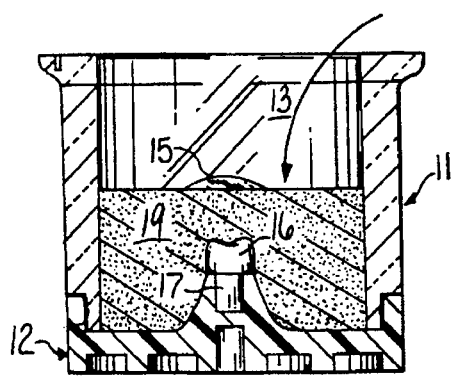
FIG. 4.
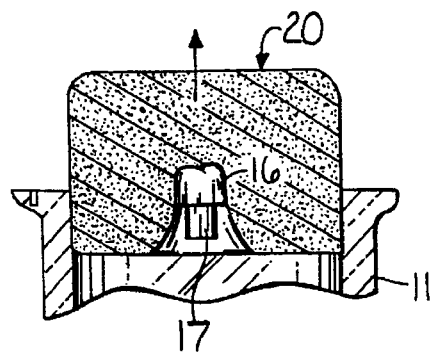
FIG. 6.
FIG. 5.

METHOD AND DEVICE FOR ELIMINATING COMPRESSION AND DISTORTION OF WAX PATTERNS IN LOST-WAX CASTING

TECHNICAL FIELD

The present invention relates generally to the art of precision molding and more particularly to a method and apparatus for accurately removing an investment mold from a lost-wax casting assembly at the conclusion of investment setting to prevent compression and distortion of the wax pattern.

BACKGROUND OF THE INVENTION

The so-called "lost-wax" method of preparing castings, and molds therefrom, are well known to the art. Particularly, use of the lost-wax method within the dental profession for the purpose of casting crowns and other such dental restorations is well known. A primary concern in forming dental castings is achieving extreme accuracy so the final product is both useful and comfortable.

One step of the lost-wax casting technique involves hardening the investment material into an investment mold through an exothermic reaction. The reaction occurs in two stages; (1) setting, when the investment material hardens into a solid, and (2) curing, additional hardening of the investment mold. The heat generated by both setting and curing causes expansion of the investment material which, when constrained by a casting assembly (e.g. casting rings and sprue formers), results in compression on and distortion of the wax pattern within the investment material. Any degree of compression against the wax pattern distorts the restoration pattern and ultimately impairs the fit of a casting produced therefrom. Thus, when the wax pattern is burned out and molten metal is introduced into the void formed within the hardened investment mold, the casting created will not correspond exactly to the original pattern. This results not only in discomfort to the patient for whom the restoration is prepared, but unnecessary expenditure of time, energy and money for the patient, the dentist, and the dental technician to modify the dimensions of the casting so it will fit reasonably comfortably and properly.

One recent innovation to reduce compression and distortion of the wax pattern is described in U.S. Pat. No. 5,183,095 to Sullivan. The assignee of the instant invention is also the assignee of the Sullivan patent. In Sullivan, the casting assembly is constructed of a clear, expandable thermoplastic. As the exothermic setting reaction proceeds, the investment material is able to expand upwardly in the casting assembly and the expandable thermoplastic gives with any axial forces from the expansion of the investment material. Unfortunately, the majority of compression forces are generated during curing when the solid investment mold is unable to expand upwardly within the casting assembly placing the expansion pressure on the casting assembly and, thus, the wax pattern. Virtually all compression forces from curing can be eliminated if the investment mold is removed from the casting assembly at the conclusion of the setting process.

SUMMARY OF THE INVENTION

With parenthetical reference to the corresponding parts, portions or surfaces of the disclosed embodiment, merely for purposes of illustration and not by way of limitation, the present invention comprises a method and device eliminating virtually all compression and distortion of a wax pattern immersed by investment material. The elimination of this compression and distortion assures the precise duplication of a tooth or dental arch.

It is known that investment material expands during curing, the process occurring after it has set into a solid investment mold. It is possible to determine the point at which the investment material becomes a solid by monitoring its temperature. Accordingly, if the investment mold can be removed from the casting assembly substantially coincident to the moment when the investment solidifies, the investment mold may then expand freely, eliminating virtually all compression and distortion of the wax pattern.

The present invention contemplates the use of a thermochromatic dye applied to a casting assembly, or blended within the material forming the casting assembly, which changes color at the temperature where the investment material solidifies.

Accordingly, a primary object of the present invention is to provide a lost-wax casting assembly having a means to indicate when investment material held reaches the temperature where it will solidify, thus, indicating to remove the investment mold for free expansion during curing, insuring the dimensional integrity of the mold produced thereby and hence the casting produced therefrom.

Another object of the present invention is to provide a method whereby a casting assembly forms the boundaries in which the investment material solidifies during setting, but is then removed, thus, allowing free expansion of the investment mold during curing.

Still a further object of the present invention is to provide a means and method of producing precisely dimensioned casting by the lost-wax method which castings are equally suitable for dental reconstructions and fine jewelry.

Yet another object of the invention is to provide a method for consistently producing precisely dimensioned castings by the lost-wax method.

These and still further objects as shall hereinafter appear are readily fulfilled by the present invention and as will be readily discerned from the following detailed description of an exemplary embodiment thereof.

BRIEF DESCRIPTION OF THE DRAWINGS

FIG. 1 is an isometric view of the device embodying the present invention for producing lost-wax castings;

FIG. 2 is a cross-sectional view of the device of FIG. 1 taken on line 2—2 thereof;

FIG. 3 is a cross-sectional view of a sprue former with a positive form in place according to the present invention;

FIG. 4 is a cross-sectional view of a casting ring connected to the sprue former of FIG. 3 and partially filled with investment solution;

FIG. 5 is a cross-sectional view of the casting device in FIG. 4 showing a further fill of investment solution; and FIG. 6 is a cross-sectional view of a cured investment mold in the process of being withdrawn from the casting ring of FIG. 5, the casting ring has been detached from the sprue former.

DESCRIPTION OF THE PREFERRED EMBODIMENTS

At the outset, it should be clearly understood that like reference numerals are intended to identify the same structural elements, portions or surfaces consistently throughout the several drawings figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

An assembly embodying the present invention is identified in the accompanying drawings by the general reference 10. Adverting to FIG. 1, each casting assembly 10 comprises a casting ring 11 and a sprue former base 12. The sprue former base has a generally conical member 14 disposed in the center thereof extending upwardly. A cylindrical cavity 18 is disposed within conical member 14 for a purpose to be hereinafter described in greater detail.

Referring now to FIG. 2, casting ring 11 connects in sealing engagement with sprue former base 12. The volume bounded by casting ring 11 and sprue former base 12 forms interior portion 13.

In the preferred embodiment, sprue former base 12 and casting ring 11 are each constructed from a transparent thermoplastic such as polyvinylchloride (PVC), polymethylmethacrylate (PMMA), polyalcrylonitrile, polypropylene and like materials having a glass transition temperature of between about 25 degrees centigrade and 105 degrees centigrade, and a melting point greater than the exothermic temperature of the chosen investment material.

As shown in FIG. 3, in one practice of the present invention, a positive wax pattern 16 made out of paraffin, or other similar material, is shaped, as by carving, to conform to the desired casting. Wax pattern 16 will have a shank or sprue 17 depending therefrom. Wax pattern 16 is then securely mounted into conical member 14 by inserting sprue 17 into cavity 18.

Adverting to FIG. 4, a solution of investment 19 is then prepared as needed and poured into interior portion 13, completely covering wax pattern 16. Investment 19 may be any of the conventional compositions commonly used for lost-wax casting. One such suitable composition is known by the brand name Belavest-T and is distributed by Leach & Dillon, Inc., North Attleboro, Mass. Belavest-T is a phosphate bound cristobalite.

Before investment mold 20 is suitably prepared for subsequent use, investment 19 must be thoroughly hardened. For convenience of explanation, the hardening of investment 19 is separated into a setting process and a curing process. The first phase comprises that time during which the investment 19 is exothermicly transformed from a liquid which has no shape, into solid investment mold 20 which is the negative of wax pattern 16 and has the external shape imparted to it by casting assembly 10. This is the setting process. As the setting process proceeds, an increase of volume of investment 19 occurs from the heat liberated increasing its volume and from the resultant products having a greater specific volume than the investment. During the setting process, while investment 19 is in a liquid form, the expansion is directed upwardly into the empty portion of interior portion 13, reducing the pressure exerted on casting assembly 10. This is shown in FIG. 5.

Once the setting process is complete, curing begins. During the curing process, the now solid investment mold 20 continues to expand, but is unable to expand upwardly to the extent non-solid investment 19 did. Accordingly, substantial pressure is exerted against the walls of casting assembly 10. Lost-wax casting assemblies are made from rigid or semi-rigid materials. As such, if curing occurs within a casting assembly, compression forces will deform wax pattern 16. This is even true when using the device described in Sullivan.

The properties of investments are well known and the point when an investment turns from liquid to solid can be determined by monitoring its temperature. For example, it is known the setting process for Belavest-T is complete when Belavest-T reaches about 112 degrees Fahrenheit to 120 degrees Fahrenheit. Thermochromatic dye indicator 15 in the preferred embodiment is Chromicolor® PVC spray paint, C/#G-7 #45 from Matsui International Co., Inc., and is known to change from a royal blue color to an orange color between 112 degrees Fahrenheit and 120 degrees Fahrenheit. Accordingly, the lab technician will know to remove investment mold 20 from casting assembly 10 at the point when the setting process concludes by monitoring the color change of thermochromatic dye indicator 15. Once investment mold 20 is removed from casting assembly 10, the expansion during the curing process may proceed freely without compression or distortion on wax pattern 16. Removal of the investment mold 20 from casting assembly 10 is shown by FIG. 6.

The Matsui dye works well with a majority of commercially available phosphate bound investments. Some commercially available investments complete the setting process at a temperature substantially above or below the 112 degrees Fahrenheit to 120 degrees Fahrenheit range. When using these investments, a thermochromatic dye changing color at the higher or lower setting temperature as appropriate should be used.

Because each investment mold 20 is removed from casting assembly 10 at the same point during the exothermic reaction, each investing mold created will have similar predictable characteristics.

An indicator means, in the preferred embodiment a dot of thermochromatic dye indicator 15 is applied directly to the exterior surface of casting assembly 10, provides a way to determine when the curing process begins. There are many other ways to apply the thermochromatic dye indicator to casting assembly 10. Self adhesive stickers treated with an appropriate thermochromatic dye can be applied to casting assembly 10. The thermochromatic dye can also be applied to the interior surface of casting assembly 10 if the casting assembly is made of a transparent material. Further, it is possibled, in some instances, to blend the thermochromatic dye into the material forming casting assembly 10. For example, the thermochromatic dye could be blended with the transparent elastic thermoplastic used in Sullivan whereby the reaching of a certain temperature would be indicated by the entire casting assembly changing color. Care must be taken to insure the thermochromatic dye indicator is applied in an appropriate position and in an appropriate size for easy visibility.

Clearly, the aforementioned applications of a thermochromatic dye indicator to a lost-wax casting assembly are not exhaustive. Other options include strips encircling the entire casting assembly and, corporate logos painted in thermochromatic dye. It is also evident the thermochromatic dye indicator can be used on any lost-wax casting assembly. The preferred embodiment discusses the casting assembly described in. Sullivan, but the thermochromatic dye indicators could be applied to traditional steel casting rings. Further, non-phosphate bound investments can be used with the present invention if thermochromatic dyes changing color at the non-phosphate bound investment's setting temperature are utilized.

From the foregoing, it is readily apparent that a useful embodiment of the present invention has been herein described and illustrated which fulfills all the aforestated objectives. It is, of course, understood that modifications, alterations and adaptations may readily occur to the artisan confronted with this disclosure and are intended within the spirit of this disclosure which is limited only by the scope of the claims appended hereto.

What is claimed is:

1. A device for producing high-precision molds for use in the preparation of lost-wax castings, comprising:

a casting assembly;

an interior portion defined by said casting assembly, said interior portion specially configured to hold investment solution;

thermochromatic dye applied to a surface of said casting assembly adapted to indicate when the temperature of said interior portion reaches the transition temperature between the setting and curing of investment solution held by said interior portion;

whereby said thermochromatic dye will indicate when investment solution held within said interior portion has reached the temperature at which the setting of investment solution concludes and curing begins.

2. The device according to claim 1 wherein said thermochromatic dye changes color at the temperature at which the setting of the investment solution concludes.

3. A device for producing high-precision molds for use in the preparation of lost-wax castings, comprising:

a casting assembly made of thermoplastic;

an interior portion defined by said casting assembly, said interior portion specially configured to hold investment solution;

thermochromatic dye blended into said casting assembly adapted to indicate when the temperature of said interior portion reaches the transition temperature between the setting and curing of investment solution held by said interior portion;

whereby said thermochromatic dye will indicate when investment solution held within said interior portion has reached the temperature at which the setting of investment solution concludes and curing begins.

4. The device according to claim 3 wherein said thermochromatic dye changes color at the temperature at which the setting of the investment solution concludes.

5. The method of ensuring consistent expansion during an exothermic reaction in an investment solution comprising the steps of:

providing a casting assembly from which lost-wax castings can be prepared, a surface of said casting assembly having thermochromatic dye applied;

placing a wax pattern in said casting assembly;

pouring an investment solution into said casting assembly, completely covering said wax pattern;

allowing said investment solution to set into a solid investment mold;

determining when said setting is complete by monitoring said thermochromatic dye;

removing said investment mold from said casting assembly when said thermochromatic dye indicates said setting is complete;

thereby the investment mold is allowed to freely further expand, eliminating compression and distortion of said wax pattern.

6. The method according to claim 5 wherein said thermochromatic dye changes color at the temperature at which the setting of the investment solution concludes.

7. The method of ensuring consistent expansion during an exothermic reaction in an investment solution comprising the steps of:

providing a casting assembly made of a thermoplastic from which lost-wax castings can be prepared, a thermochromatic dye blended into said casting assembly;

placing a wax pattern in said casting assembly;

pouring an investment solution into said casting assembly, completely covering said wax pattern;

allowing said investment solution to set into a solid investment mold;

determining when said setting is complete by monitoring said thermochromatic dye;

removing said investment mold from said casting assembly when said thermochromatic dye indicates said setting is complete;

thereby the investment mold is allowed to freely further expand, eliminating compression and distortion of said wax pattern.

8. The method according to claim 7 wherein the thermochromatic dye changes color at the temperature at which the setting of the investment solution concludes.

* * * * *